United States Patent
Crisostomo et al.

(10) Patent No.: US 10,335,277 B2
(45) Date of Patent: Jul. 2, 2019

(54) ADJUSTABLE NOSECONE

(71) Applicant: BOSTON SCIENTIFIC SCIMED, INC., Maple Grove, MN (US)

(72) Inventors: Crissly V. Crisostomo, Folsom, CA (US); Randy S. Gamarra, Santa Clara, CA (US)

(73) Assignee: BOSTON SCIENTIFIC SCIMED INC., Maple Grove, MN (US)

(*) Notice: Subject to any disclaimer, the term of this patent is extended or adjusted under 35 U.S.C. 154(b) by 267 days.

(21) Appl. No.: 15/197,893

(22) Filed: Jun. 30, 2016

(65) Prior Publication Data

US 2017/0000607 A1 Jan. 5, 2017

Related U.S. Application Data

(60) Provisional application No. 62/188,223, filed on Jul. 2, 2015.

(51) Int. Cl.
*A61F 2/95* (2013.01)
*A61F 2/24* (2006.01)

(52) U.S. Cl.
CPC .............. *A61F 2/2436* (2013.01); *A61F 2/24* (2013.01); *A61F 2/2412* (2013.01); *A61F 2/95* (2013.01); *A61F 2002/9517* (2013.01)

(58) Field of Classification Search
CPC ........................ A61F 2/2436; A61F 2002/9517
See application file for complete search history.

(56) References Cited

U.S. PATENT DOCUMENTS

| 15,192 | A | 6/1856 | Peale |
| 2,682,057 | A | 6/1954 | Lord |
| 2,701,559 | A | 2/1955 | Cooper |
| 2,832,078 | A | 4/1958 | Williams |
| 3,099,016 | A | 7/1963 | Edwards |
| 3,113,586 | A | 12/1963 | Edmark, Jr. |

(Continued)

FOREIGN PATENT DOCUMENTS

| CN | 1338951 A | 3/2002 |
| DE | 19532846 A1 | 3/1997 |

(Continued)

OTHER PUBLICATIONS

International Search Report and Written Opinion PCT/US/2016/040404, dated Oct. 26, 2016.

(Continued)

*Primary Examiner* — Amy R Weisberg
(74) *Attorney, Agent, or Firm* — Seager, Tufte & Wickhem LLP

(57) ABSTRACT

A percutaneous valve delivery system may include an outer sheath and an inner catheter disposed within the outer sheath. The inner catheter may include a plurality of lumens formed therein. A tubular extension may extend distally from a distal end of the inner catheter, wherein the tubular extension is axially movable relative to the inner catheter. A nose cone may be attached to the tubular extension. A handle may be attached to the outer sheath, wherein the handle is configured to shift the outer sheath between a first position and a second position relative to the inner catheter. A valve replacement implant may be releasably coupled to the inner catheter.

18 Claims, 11 Drawing Sheets

(56) References Cited

U.S. PATENT DOCUMENTS

| | | |
|---|---|---|
| 3,130,418 A | 4/1964 | Head et al. |
| 3,143,742 A | 8/1964 | Cromie |
| 3,334,629 A | 8/1967 | Cohn |
| 3,367,364 A | 2/1968 | Cruz, Jr. et al. |
| 3,409,013 A | 11/1968 | Berry |
| 3,445,916 A | 5/1969 | Schulte |
| 3,540,431 A | 11/1970 | Mobin-Uddin |
| 3,548,417 A | 12/1970 | Kischer et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Van Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | Dipisa, Jr. |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,035,686 A * | 7/1991 | Crittenden ........ A61M 25/0169 285/334.4 |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,903 A * | 11/1992 | Crittenden ........ A61M 25/0169 604/103.09 |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,483 A | 6/1993 | Tower |
| 5,238,004 A | 8/1993 | Sahatjian et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,500,014 A | 3/1996 | Quijano et al. |
| 5,507,767 A | 4/1996 | Maeda et al. |
| 5,534,007 A | 7/1996 | St. Germain et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |

(56) References Cited

U.S. PATENT DOCUMENTS

| | | |
|---|---|---|
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,772,609 A | 6/1998 | Nguyen et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,051,014 A | 4/2000 | Jang |
| 6,059,827 A | 5/2000 | Fenton, Jr. |
| 6,074,418 A | 6/2000 | Buchanan et al. |
| 6,093,203 A | 7/2000 | Uflacker |
| 6,096,074 A | 8/2000 | Pedros |
| 6,123,723 A | 9/2000 | Konya et al. |
| 6,132,473 A | 10/2000 | Williams et al. |
| 6,139,510 A | 10/2000 | Palermo |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsuigita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | De Paulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,402,736 B1 | 6/2002 | Brown et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Don Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,803 B1 | 1/2003 | Horikawa et al. |
| 6,508,833 B1 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,569,196 B1 | 5/2003 | Vesely |

(56) References Cited

U.S. PATENT DOCUMENTS

| | | |
|---|---|---|
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford, III et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,769,434 B2 | 8/2004 | Liddicoat et al. |
| 6,773,454 B2 | 8/2004 | Wholey et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,814,746 B2 | 11/2004 | Thompson et al. |
| 6,821,297 B2 | 11/2004 | Snyders |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,097,658 B2 | 8/2006 | Oktay |
| 7,122,020 B2 | 10/2006 | Mogul |
| 7,125,418 B2 | 10/2006 | Duran et al. |
| 7,141,063 B2 | 11/2006 | White et al. |
| 7,166,097 B2 | 1/2007 | Barbut |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,258,696 B2 | 8/2007 | Rabkin et al. |
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 | 11/2008 | Salahieh et al. |
| 7,470,285 B2 | 12/2008 | Nugent et al. |
| 7,491,232 B2 | 2/2009 | Bolduc et al. |
| 7,510,574 B2 | 3/2009 | Lê et al. |
| 7,524,330 B2 | 4/2009 | Berreklouw |
| 7,530,995 B2 | 5/2009 | Quijano et al. |
| 7,544,206 B2 | 6/2009 | Cohn |
| 7,622,276 B2 | 11/2009 | Cunanan et al. |
| 7,628,803 B2 | 12/2009 | Pavcnik et al. |
| 7,632,298 B2 | 12/2009 | Hijikema et al. |
| 7,674,282 B2 | 3/2010 | Wu et al. |
| 7,712,606 B2 | 5/2010 | Salahieh et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |
| 7,846,204 B2 | 12/2010 | Letac et al. |
| 7,871,430 B2 * | 1/2011 | Pavcnik .............. A61F 2/2436 623/1.11 |
| 7,892,292 B2 | 2/2011 | Stack et al. |
| 7,918,880 B2 | 4/2011 | Austin |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |

(56) References Cited

U.S. PATENT DOCUMENTS

| | | |
|---|---|---|
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,157,853 B2 | 4/2012 | Laske et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,308,798 B2 | 11/2012 | Pintor et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson, IV et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0058995 A1 | 5/2002 | Stevens |
| 2002/0077696 A1 | 6/2002 | Ladno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |

(56) References Cited

U.S. PATENT DOCUMENTS

| | | |
|---|---|---|
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | Wasdyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0167955 A1* | 7/2007 | Arnault De La Menardiere ........ A61F 2/954 606/108 |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0082165 A1 | 4/2008 | Wilson et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0269878 A1 | 10/2008 | Iobbi |
| 2008/0288054 A1 | 11/2008 | Pulnev et al. |
| 2009/0005863 A1 | 1/2009 | Goetz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |
| 2009/0093877 A1 | 4/2009 | Keidar et al. |
| 2009/0171456 A1 | 7/2009 | Kveen et al. |
| 2009/0222076 A1 | 9/2009 | Figulla et al. |

(56) References Cited

U.S. PATENT DOCUMENTS

| | | | |
|---|---|---|---|
| 2009/0264759 A1 | 10/2009 | Byrd | |
| 2009/0264997 A1 | 10/2009 | Salahieh et al. | |
| 2009/0299462 A1 | 12/2009 | Fawzi et al. | |
| 2010/0030318 A1* | 2/2010 | Berra | A61F 2/07 623/1.11 |
| 2010/0049313 A1 | 2/2010 | Alon et al. | |
| 2010/0094399 A1 | 4/2010 | Dorn et al. | |
| 2010/0121434 A1 | 5/2010 | Paul et al. | |
| 2010/0191326 A1 | 7/2010 | Alkhatib | |
| 2010/0219092 A1 | 9/2010 | Salahieh et al. | |
| 2010/0280495 A1 | 11/2010 | Paul et al. | |
| 2011/0257733 A1 | 10/2011 | Dwork | |
| 2011/0257735 A1 | 10/2011 | Salahieh et al. | |
| 2011/0276129 A1 | 11/2011 | Salahieh et al. | |
| 2012/0016469 A1 | 1/2012 | Salahieh et al. | |
| 2012/0016471 A1 | 1/2012 | Salahieh et al. | |
| 2012/0022642 A1 | 1/2012 | Haug et al. | |
| 2012/0029627 A1 | 2/2012 | Salahieh et al. | |
| 2012/0041549 A1 | 2/2012 | Salahieh et al. | |
| 2012/0041550 A1 | 2/2012 | Salahieh et al. | |
| 2012/0046740 A1 | 2/2012 | Paul et al. | |
| 2012/0053683 A1 | 3/2012 | Salahieh et al. | |
| 2012/0089224 A1 | 4/2012 | Haug et al. | |
| 2012/0132547 A1 | 5/2012 | Salahieh et al. | |
| 2012/0197379 A1 | 8/2012 | Laske et al. | |
| 2012/0203325 A1* | 8/2012 | Weisman | A61F 2/95 623/1.12 |
| 2012/0330409 A1 | 12/2012 | Haug et al. | |
| 2013/0013057 A1 | 1/2013 | Salahieh et al. | |
| 2013/0018457 A1 | 1/2013 | Gregg et al. | |
| 2013/0030520 A1 | 1/2013 | Lee et al. | |
| 2013/0123795 A1* | 5/2013 | Gamarra | A61B 17/00234 606/108 |
| 2013/0123796 A1 | 5/2013 | Sutton et al. | |
| 2013/0158653 A1* | 6/2013 | Gamarra | A61F 2/2436 623/2.11 |
| 2013/0158656 A1 | 6/2013 | Sutton et al. | |
| 2013/0190865 A1 | 7/2013 | Anderson | |
| 2013/0304199 A1 | 11/2013 | Sutton et al. | |
| 2014/0018911 A1 | 1/2014 | Zhou et al. | |
| 2014/0094904 A1 | 4/2014 | Salahieh et al. | |
| 2014/0114405 A1 | 4/2014 | Paul et al. | |
| 2014/0114406 A1 | 4/2014 | Salahieh et al. | |
| 2014/0121766 A1 | 5/2014 | Salahieh et al. | |
| 2014/0135912 A1 | 5/2014 | Salahieh et al. | |
| 2014/0243967 A1 | 8/2014 | Salahieh et al. | |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0144167 B1 | 11/1989 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1088529 A2 | 4/2001 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1430853 A2 | 6/2004 |
| EP | 1472996 A1 | 11/2004 |
| EP | 1229864 B1 | 4/2005 |
| EP | 1059894 B1 | 7/2005 |
| EP | 1078610 B1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1469797 B1 | 11/2005 |
| EP | 1600121 A1 | 11/2005 |
| EP | 1156757 B1 | 12/2005 |
| EP | 1616531 A2 | 1/2006 |
| EP | 1605871 B1 | 7/2008 |
| FR | 2788217 A1 | 7/2000 |
| GB | 2056023 A | 3/1981 |
| GB | 2398245 A | 8/2004 |
| SU | 1271508 A1 | 11/1986 |
| SU | 1371700 A1 | 2/1988 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9829057 A1 | 7/1998 |
| WO | 9836790 A1 | 8/1998 |
| WO | 9850103 A1 | 11/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 0009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0149213 A2 | 7/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0197715 A1 | 12/2001 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 02056955 A1 | 7/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03028592 A1 | 4/2003 |
| WO | 03030776 A2 | 4/2003 |
| WO | 03037227 A2 | 5/2003 |
| WO | 03045275 A2 | 6/2003 |
| WO | 03047648 A2 | 6/2003 |
| WO | 03015851 B1 | 11/2003 |
| WO | 03094793 A1 | 11/2003 |
| WO | 03094797 A1 | 11/2003 |
| WO | 2004006803 A1 | 1/2004 |
| WO | 2004006804 A1 | 1/2004 |
| WO | 2004014256 A2 | 2/2004 |
| WO | 2004019811 A2 | 3/2004 |
| WO | 2004019817 A1 | 3/2004 |
| WO | 2004021922 A2 | 3/2004 |
| WO | 2004023980 A2 | 3/2004 |
| WO | 2004026117 A2 | 4/2004 |
| WO | 2004041126 A1 | 5/2004 |
| WO | 2004043293 A2 | 5/2004 |

(56) References Cited

FOREIGN PATENT DOCUMENTS

| | | |
|---|---|---|
| WO | 2004047681 A1 | 6/2004 |
| WO | 2004058106 A2 | 7/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |
| WO | 2005009285 A2 | 2/2005 |
| WO | 2005011534 A1 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005062980 A2 | 7/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2006138391 A2 | 12/2006 |
| WO | 2007033093 A2 | 3/2007 |
| WO | 2007035471 A2 | 3/2007 |
| WO | 2007044285 A2 | 4/2007 |
| WO | 2007053243 A2 | 5/2007 |
| WO | 2007058847 A2 | 5/2007 |
| WO | 2007092354 A2 | 8/2007 |
| WO | 2007097983 A2 | 8/2007 |
| WO | 2010042950 A2 | 4/2010 |
| WO | 2012116368 A2 | 8/2012 |
| WO | 2013070569 A1 | 5/2013 |
| WO | 2014122205 A1 | 8/2014 |
| WO | 2015063118 A1 | 5/2015 |

OTHER PUBLICATIONS

Andersen et al., "Transluminal implantation of artificial heart valves. Description of a new expandable aortic valve and initial results with implantation by catheter technique in closed chest pigs." Euro. Heart J., 13:704-708, May 1992.
Atwood et al., "Insertion of Heart Valves by Catheterization." Project Supervised by Prof. S. Muftu of Northeastern University 2001-2002: 36-40, May 30, 2002.
Bodnar et al., "Replacement Cardiac Valves R Chapter 13: Extinct Cardiac Valve Prostheses" Pergamon Publishing Corporation. New York, 307-322, 1991.
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implementation of an Aortic Valve Prosthesis for Calcitic Aortic Stenosis: First Human Case Description." Circulation, 106: 3006-3008, Dec. 10, 2002.
Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.
Ferrari et al., "Percutaneous Transvascular Aortic Valve Replacement with Self-Expanding Stent-Valve Device." Poster from the presentation given at SMIT 2000, 12th International Conference. Sep. 5, 2000.
Hijazi, "Transcatheter Valve Replacement: A New Era of Percutaneous Cardiac Intervention Begins." J. of Am. College of Cardio., 43(6): 1088-1089, Mar. 17, 2004.
Huber et al., "Do Valved Stents Compromise Coronary Flow?" European Journal of Cardio-thoracic Surgery, vol. 25: 754-759, Jan. 23, 2004.
Knudsen et al., "Catheter-implanted prosthetic heart valves." Int'l J. of Art. Organs, 16(5): 253-262, May 1993.
Kort et al., "Minimally Invasive Aortic Valve Replacement: Echocardiographic and Clinical Results." Am. Heart J., 142(3): 476-481, Sep. 2001.
Love et al., The Autogenous Tissue Heart Valve: Current Status. Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.
Moulopoulos et al., "Catheter-Mounted Aortic Valves." Annals of Thoracic Surg., 11(5): 423-430, May 1971.
Paniagua et al., "Percutaneous Heart Valve in the Chronic in Vitro Testing Model." Circulation, 106: e51-e52, Sep. 17, 2002.
Paniagua et al., "Heart Watch." Texas Heart Institute. Edition: 8 pages, Spring, 2004.
Pavcnik et al., "Percutaneous Bioprosthetic Venous Valve: A Long-term Study in Sheep." J. of Vascular Surg., 35(3):598-603, Mar. 2002.
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Sochman et al., "Percutaneous Transcatheter Aortic Disc Valve Prosthesis Implantation: A Feasibility Study." Cardiovasc. Intervent. Radiol., 23: 384-388, Sep. 2000.
Stuart, "In Heart Valves, A Brave, New Non-Surgical World." Start-Up. 9-17, Feb. 2004.
Vahanian et al., "Percutaneous Approaches to Valvular Disease." Circulation, 109: 1572-1579, Apr. 6, 2004.
Van Herwerden et al., "Percutaneous Valve Implantation: Back to the Future?" Euro. Heart J., 23(18): 1415-1416, Sep. 2002.
Zhou et al, "Self-expandable Valved Stent of Large Size: Off-Bypass Implantation in Pulmonary Position." Eur. J. Cardiothorac, 24: 212-216, Aug. 2003.
Examiner's First Report on AU Patent Application No. 2011202667, dated May 17, 2012.
"A Matter of Size." Triennial Review of the National Nanotechnology Initiative, The National Academies Press, Washington DC, v-13, http://www.nap.edu/catalog/11752/a-matter-of-size-triennial-review-of-the-national-nanotechnology, 2006.
Atwood et al., "Insertion of Heart Valves by Catheterization." The Capstone Design Course Report MIME 1501-1502. Technical Design Report Northeastern University, pp. 1-93, Nov. 5, 2007.
Supplemental Search Report from EP Patent Office, EP Application No. 04813777.2, dated Aug. 19, 2011.
Supplemental Search Report from EP Patent Office, EP Application No. 04815634.3, dated Aug. 19, 2011.
Cunanan et al., "Tissue Characterization and Calcification Potential of Commercial Bioprosthetic Heart Valves." Ann. Thorac. Surg., S417-421, May 15, 2001.
Cunliffe et al., "Glutaraldehyde Inactivation of Exotic Animal Viruses in Swine Heart Tissue." Applied and Environmental Microbiology, Greenport, New York, 37(5): 1044-1046, May 1979.
EP Search Report for EP Application No. 06824992.9, dated Aug. 10, 2011.

(56) References Cited

OTHER PUBLICATIONS

"Heart Valve Materials—Bovine (cow)." Equine & Porcine Pericardium, Maverick Biosciences Pty. Lt, http://maverickbio.com/biological-medical-device-materials.php?htm. 2009.

Helmus, "Mechanical and Bioprosthetic Heart Valves in Biomaterials for Artificial Organs." Woodhead Publishing Limited: 114-162, 2011.

Hourihan et al., "Transcatheter Umbrella Closure of Valvular and Paravalvular Leaks." JACC, Boston, Massachusetts, 20(6): 1371-1377, Nov. 15, 1992.

Laborde et al., "Percutaneous Implantation of the Corevalve Aortic Valve Prosthesis for Patients Presenting High Risk for Surgical Valve Replacement." EuroIntervention: 472-474, Feb. 2006.

Levy, "*Mycobacterium chelonei* Infection of Porcine Heart Valves." The New England Journal of Medicine, Washington DC, 297(12), Sep. 22, 1977.

Supplemental Search Report from EP Patent Office, EP Application No. 05758878.2, dated Oct. 24, 2011.

"Pericardial Heart Valves." Edwards Lifesciences, Cardiovascular Surgery FAQ, http://www.edwards.com/products/cardiovascularsurgeryfaq.htm, Nov. 14, 2010.

Southern Lights Biomaterials Homepage, http://www.slv.co.nz/, Jan. 7, 2011.

Stassano. "Mid-term Results of the Valve-on-Valve Technique for Bioprosthetic Failure." European Journal of Cardiothoracic Surgery: vol. 18, 453-457, Oct. 2000.

Topol. "Percutaneous Expandable Prosthetic Valves." Textbook of Interventional Cardiology, W.B. Saunders Company, 2: 1268-1276, 1994.

\* cited by examiner

ADJUSTABLE NOSECONE

RELATED APPLICATIONS

This application claims priority to U.S. Provisional Application No. 62/188,223, filed Jul. 2, 2015.

TECHNICAL FIELD

The present disclosure pertains to medical devices, and methods for manufacturing medical devices. More particularly, the present disclosure pertains to medical devices for delivering a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

In a first aspect, a percutaneous valve delivery system may comprise an outer sheath, an inner catheter disposed within the outer sheath, the inner catheter including a plurality of lumens formed therein, a tubular extension extending distally from a distal end of the inner catheter, wherein the tubular extension is axially movable relative to the inner catheter, a nose cone attached to the tubular extension, a handle attached to the outer sheath, wherein the handle is configured to shift the outer sheath between a first position and a second position relative to the inner catheter, and a valve replacement implant releasably coupled to the inner catheter.

In addition or alternatively, and in a second aspect, the tubular extension is fixedly attached to a hypotube slidably received within one of the plurality of lumens.

In addition or alternatively, and in a third aspect, the percutaneous valve delivery system may further comprise a luer connector attached to a proximal end of the hypotube, the luer connector being configured to engage a proximal end of the handle.

In addition or alternatively, and in a fourth aspect, the luer connector, the hypotube, the tubular extension, and the nose cone together form a nose cone subassembly having a guidewire lumen extending through the percutaneous valve delivery system, wherein the guidewire lumen is configured to slidably receive a guidewire therein.

In addition or alternatively, and in a fifth aspect, the luer connector is threadably attached to the proximal end of the hypotube.

In addition or alternatively, and in a sixth aspect, the luer connector includes a protrusion preventing distal axial movement of the luer connector past the proximal end of the handle.

In addition or alternatively, and in a seventh aspect, the nose cone subassembly is axially movable relative to the inner catheter and the handle.

In addition or alternatively, and in an eighth aspect, the valve replacement implant is disposed about the tubular extension.

In addition or alternatively, and in a ninth aspect, the nose cone is fixedly attached at a distal end of the tubular extension.

In addition or alternatively, and in a tenth aspect, a proximal portion of the nose cone is configured to matingly engage a distal end of the outer sheath in the first position.

In addition or alternatively, and in an eleventh aspect, a percutaneous valve delivery system may comprise an outer sheath, an inner catheter disposed within the outer sheath, the inner catheter including a plurality of lumens formed therein, a tubular extension extending distally from a distal end of the inner catheter, wherein the tubular extension is axially movable relative to the inner catheter, a nose cone attached to the tubular extension, a handle attached to the outer sheath, wherein the handle is configured to shift the outer sheath between a first position and a second position relative to the inner catheter, the inner catheter being fixed to the handle, and a valve replacement implant releasably coupled to the inner catheter, the tubular extension extending through the valve replacement implant.

In addition or alternatively, and in a twelfth aspect, the tubular extension is fixedly attached to a hypotube slidably received within one of the plurality of lumens.

In addition or alternatively, and in a thirteenth aspect, a percutaneous valve delivery system may further comprise a luer connector attached to a proximal end of the hypotube, the luer connector being configured to engage a proximal end of the handle.

In addition or alternatively, and in a fourteenth aspect, the luer connector, the hypotube, the tubular extension, and the nose cone together form a nose cone subassembly having a guidewire lumen extending through the percutaneous valve delivery system, wherein the guidewire lumen is configured to slidably receive a guidewire therein.

In addition or alternatively, and in a fifteenth aspect, the luer connector is threadably attached to the proximal end of the hypotube.

In addition or alternatively, and in a sixteenth aspect, the luer connector includes a protrusion preventing distal axial movement of the luer connector past the proximal end of the handle.

In addition or alternatively, and in a seventeenth aspect, the nose cone subassembly is axially movable relative to the inner catheter and the handle.

In addition or alternatively, and in an eighteenth aspect, the nosecone is fixedly attached at a distal end of the tubular extension.

In addition or alternatively, and in a nineteenth aspect, a proximal portion of the nose cone is configured to abut a distal end of the outer sheath in the first position.

In addition or alternatively, and in a twentieth aspect, the nose cone is spaced distally from the outer sheath in the second position.

The above summary of some embodiments is not intended to describe each disclosed embodiment or every implementation of the present invention. The Figures, and Detailed Description, which follow, more particularly exemplify these embodiments.

Figure 1:
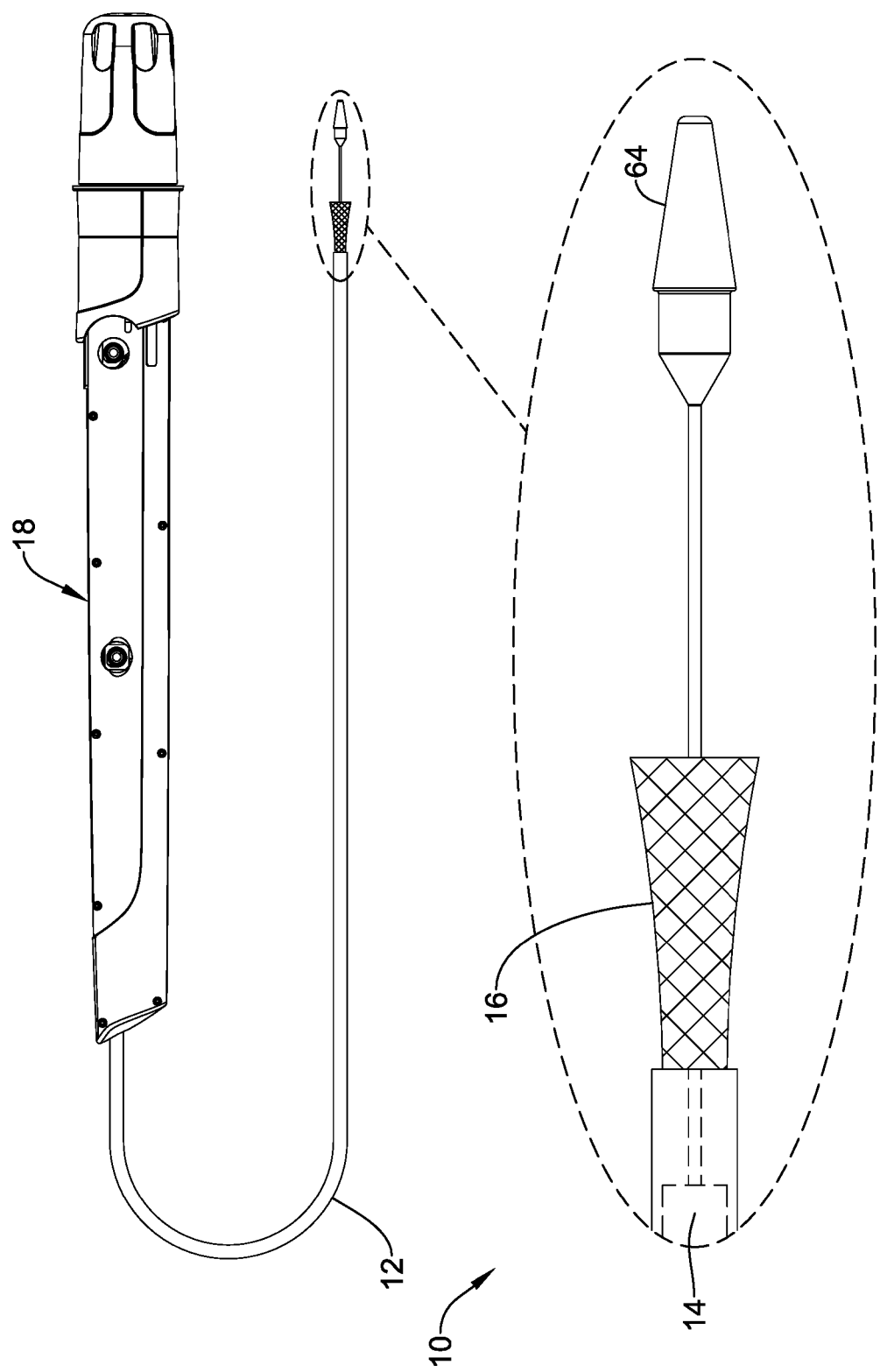
FIG. 1 is side view of an example valve delivery system.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally be considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. Other relative terms, such as "upstream" and "downstream" refer to a direction of fluid flow within a lumen, such as a body lumen or blood vessel.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve can have a serious effect on a human and could lead to serious health condition and/or death if not dealt with. Treatment of defective heart valves poses other challenges in that the treatment often requires the repair or outright replacement of the defective valve.

Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve). In addition, the devices disclosed herein may deliver the replacement heart valve percutaneously and, thus, may be much less invasive to the patient. The devices disclosed herein may also provide a number of additional desirable features and benefits as described in more detail below.

FIG. 1 is a side view of an example valve delivery system 10. It should be noted that some features of the valve delivery system 10 are either not shown, or are shown schematically, in FIG. 1 for simplicity. Additional details regarding some of the components of the valve delivery system 10 are provided in other figures in greater detail. The valve delivery system 10 may be used to deliver and/or deploy a variety of medical devices to a number of locations within the anatomy. In at least some embodiments, the valve delivery system 10 is a replacement heart valve delivery system (e.g., a replacement aortic valve delivery system) that can be used for percutaneous delivery of a replacement heart valve. This, however, is not intended to be limiting as the valve delivery system 10 may also be used for other interventions including mitral valve replacement, valve repair, valvuloplasty, and the like, or other similar interventions.

Figure 3:
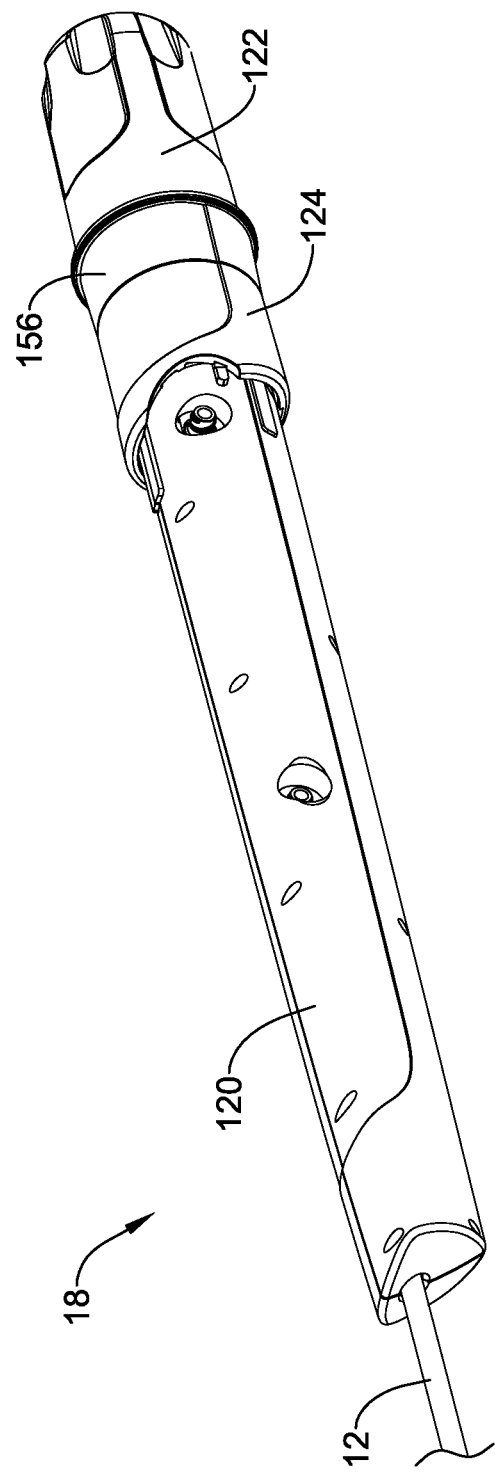
FIG. 3 is a partial perspective view of a portion of the example valve delivery system of FIG. 1.
Figure 4:
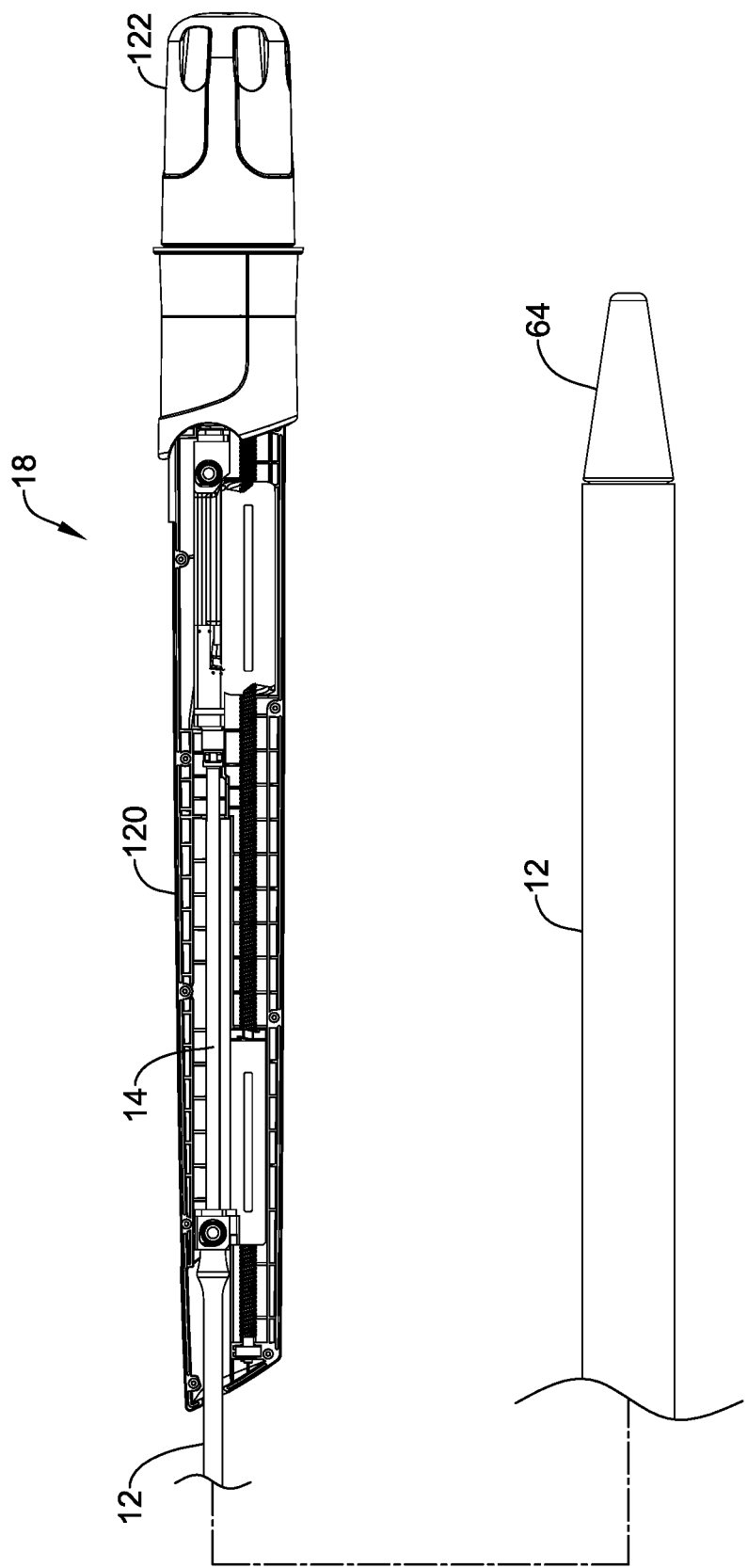
FIG. 4 is a partial cut-away side view of the example valve delivery system of FIG. 1.
Figure 5:
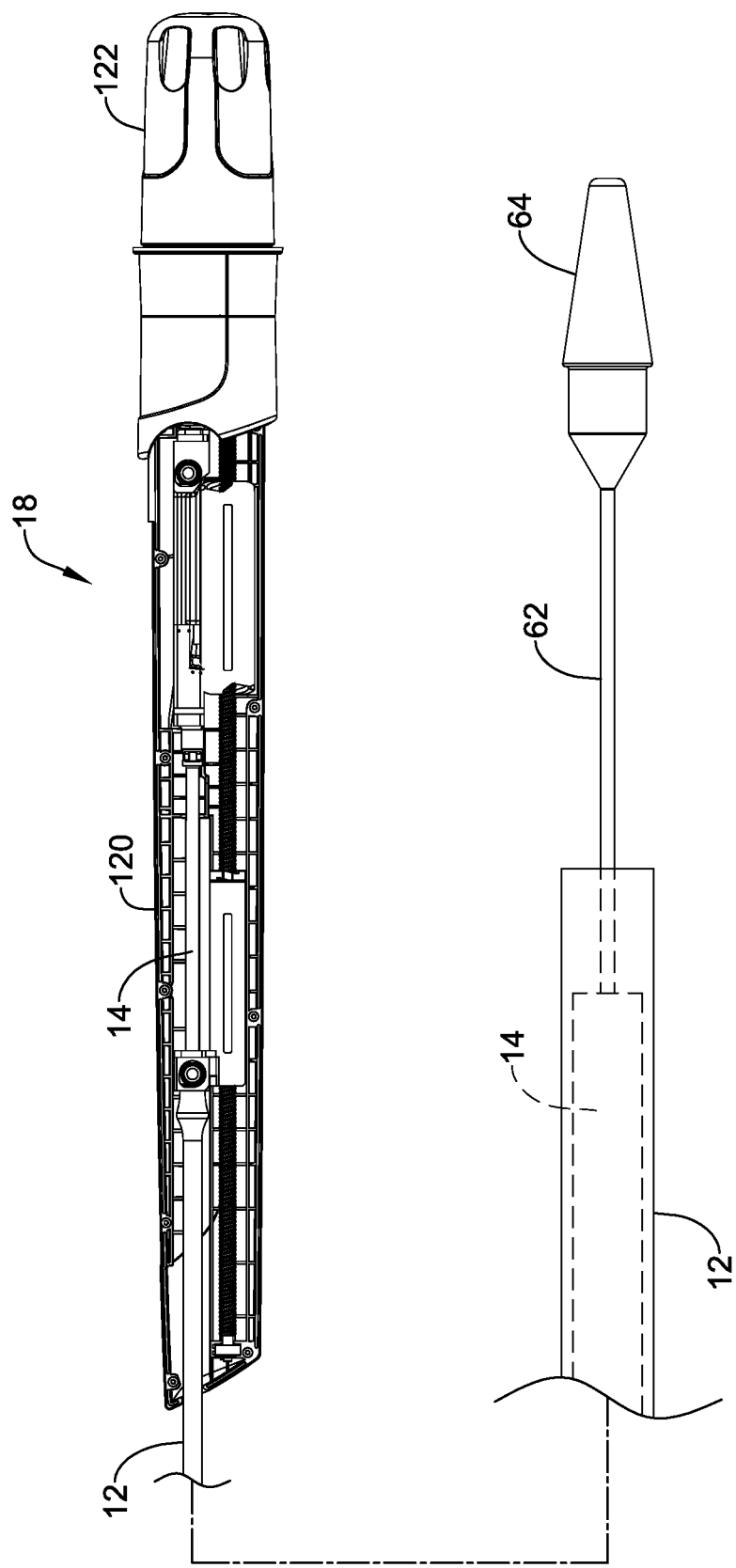
FIG. 5 is a partial cut-away side view of the example valve delivery system of FIG. 1.

In some embodiments, the valve delivery system 10 may generally be described as a catheter system that includes an outer sheath 12 and an inner catheter 14 (a portion of which is shown in FIG. 1 in phantom line) disposed within and/or extending at least partially through the outer sheath 12. In some embodiments, a valve replacement implant 16 may be releasably coupled to the inner catheter 14 and disposed within the outer sheath 12 during delivery of the valve replacement implant 16. In some embodiments, a device handle 18 may be disposed at, attached to, and/or coupled to a proximal end of the outer sheath 12 and the inner catheter 14, as seen in FIGS. 3-5 for example. In some embodiments, the outer sheath 12 may be axially translatable relative to the device handle 18 and/or the inner catheter 14. In some embodiments, the inner catheter 14 may be fixedly attached to and/or fixed in position relative to the device handle 18. In general, the device handle 18 may be configured to shift (i.e., translate, move, reposition, etc.) the outer sheath 12 between a first position and a second position relative to the inner catheter 14, as well as aid in the deployment of the valve replacement implant 16.

In use, the valve delivery system 10 may be advanced percutaneously through a patient's vasculature to a position adjacent to an area of interest. For example, valve delivery system 10 may be advanced through the vasculature to a position adjacent to a defective aortic valve. During delivery, the valve replacement implant 16 may be generally disposed in an elongated and low profile "delivery" configuration at, coupled to, and/or within the outer sheath 12 distally of the inner catheter 14, wherein the outer sheath 12 is disposed at a first position relative to the inner catheter. Once positioned, the device handle 18 may be actuated to proximally retract the outer sheath 12 to a second position relative to the inner catheter 14, which may be held stationary by the device handle 18, to expose the valve replacement implant 16. The valve replacement implant 16 may be actuated in order to expand implant into a generally shortened and larger profile "deployed" configuration suitable for implantation within the anatomy. After the valve replacement implant 16 is suitably deployed within the anatomy, the valve replacement implant 16 may be released and/or detached from the valve delivery system 10, and the valve delivery system 10 may be removed from the vasculature, leaving the valve replacement implant 16 in place to function as, for example, a suitable replacement for the native aortic valve. In at least some interventions, the valve replacement implant 16 may be deployed within the native aortic valve (e.g., the native valve is left in place and not excised). Alternatively, the native aortic valve may be removed (e.g., such as through valvuloplasty, for example) and the valve replacement implant 16 may be deployed in its place as a replacement.

In some embodiments, the outer sheath 12 may define a proximal portion and a distal portion. In some embodiments, the distal portion may have a slightly enlarged or flared inner diameter, which may provide additional space for holding the medical device implant therein. In some embodiments, an inner diameter of the outer sheath 12 along the proximal portion may be in the range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.56388±0.0508 cm (0.222±0.002 inches). In some embodiments, an inner diameter of the outer sheath 12 along the distal portion may be in the range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.579 to 0.5842 cm (0.228 to 0.230 inches). In some embodiments, at the distal end of the distal portion may be a distal tip, which may be flared or otherwise have a funnel-like shape. The funnel-like shape may increase the outer diameter (and the inner diameter) of the outer sheath 12 at the distal tip and in some embodiments may aid in the sheathing and/or re-sheathing of the medical device implant into the outer sheath 12. In some embodiments, other than at the distal tip, the outer sheath 12 may have a generally constant outer diameter. For example, the outer sheath 12 may have an outer diameter in the range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.6858 cm (0.270 inches). These are just examples. Other embodiments are contemplated that have differing dimensions (including those appropriate for differently sized patients including children) and/or arrangements for the outer diameter and/or the inner diameter of the outer sheath 12.

These contemplated embodiments include delivery sheaths with flared or otherwise variable outer diameters, embodiments with constant inner diameters, combinations thereof, and the like. In some embodiments, the outer sheath 12 may also have a length that is appropriate for reaching the intended area of interest within the anatomy. For example, in some embodiments, the outer sheath 12 may have a length in the range of about 30 to 200 cm, or about 60 to 150 cm, or about 100 to 120 cm, or about 108±0.20 cm. In some embodiments, the outer sheath 12 and/or one or more portions of the outer sheath 12 may be curved. For example, in some embodiments, the distal portion of the outer sheath 12 may be curved. In one example, a radius of the curved distal portion (as measured from a central axis of the outer sheath 12) may be in the range of about 2 to 6 cm (20 to 60 mm), or about 3 to 4 cm (30 to 40 mm), or about 3.675 cm (36.75 mm). Again, these dimensions are examples and are not intended to be limiting.

In some embodiments, the outer sheath 12 may be formed from a singular monolithic tube or unitary member. Alternatively, the outer sheath 12 may include a plurality of layers or portions. One or more of these layers may include a reinforcing structure such as a braid, coil, mesh, combinations thereof, or the like. For example, in some embodiments, the outer sheath 12 may include an inner liner or layer. In some embodiments, an intermediate or tier layer may be disposed on the inner liner. In some embodiments, a reinforcement may be disposed on the intermediate layer. In some embodiments, a topcoat or outer layer may be disposed on or over the reinforcement. In some embodiments, an outer coating (e.g., a lubricious coating, a hydrophilic coating, a hydrophobic coating, etc.) may be disposed on, over, and/or along portions or all of the topcoat or outer layer. These are just examples. Several alternative structural configurations are contemplated for the outer sheath 12 including embodiments including two or more layers that may be different, embodiments without a reinforcement, and the like, or other suitable configurations.

The dimensions and materials utilized for the various layers of the outer sheath 12 may also vary. For example, an inner liner may include a polymeric material such as fluorinated ethylene propylene (FEP) and may have a thickness in the range of about 0.00254 to 0.0127 cm (0.001 to 0.005 inches) or about 0.00762±0.00254 (0.003±0.001 inches), an intermediate layer may include a polymer material such as polyether block amide (e.g., PEBAX 6333) and may have a thickness in the range of about 0.00254 to 0.0127 cm (0.001 to 0.005 inches) or about 0.00508±0.00254 (0.002±0.001 inches), an outer coating may include a polymer material such as polyether block amide (e.g., PEBAX 7233) and may have a thickness in the range of about 0.00254 to 0.0254 cm (0.001 to 0.01 inches). In some embodiments, an outer coating may vary in thickness. For example, along a proximal portion, an outer coating may have greater thickness, such as about 0.0127 to about 0.0508 cm or about 0.02159 cm (0.005 to 0.02 inches or about 0.0085 inches), than along a distal portion and/or at a distal tip, which may be about 0.0127 to about 0.0508 cm or about 0.01651 cm (e.g., about 0.005 to 0.02 inches or about 0.0065 inches). These are just examples as other suitable materials may be used.

A reinforcement may also vary in form. In at least some embodiments, a reinforcement may take the form of a braid, coil, mesh, or the like. For example, in some embodiments, a reinforcement may include a metallic braid (e.g., stainless steel). In some of these embodiments, a reinforcement may also include additional structures such as one or more longitudinally-extending strands. For example, a reinforcement may include a pair of longitudinally-extending aramid and/or para aramid strands (for example, KEVLAR®) disposed on opposite sides of the braid. In some embodiments, these strands may or may not be woven into portions or all of the braid.

In some embodiments, a distal end region of the inner catheter 14 may include a step in outer diameter that defines a decreased outer diameter section. For example, a decreased outer diameter section may have an outer diameter in the range of about 0.127 to 0.635 cm (0.05 to 0.25 inches), or about 0.254 to 0.508 cm (0.10 to 0.20 inches), or about 0.38608±0.00762 (0.152±0.003 inches) as opposed to the remainder of the inner catheter 14 where the outer diameter may be in the range of about 0.127 to 0.762 cm (0.05 to 0.30 inches), or about 0.254 to 0.635 cm (0.10 to 0.25 inches), or about 0.508±0.0254 cm (0.20±0.01 inches). The decreased outer diameter section may define a region where other components of the valve delivery system 10 may be attached.

In some embodiments, the inner catheter 14 may include a plurality of lumens formed therein. In some embodiments, the inner catheter 14 may be formed as an extruded polymeric shaft. Other forms are also contemplated including other polymer shafts or tubes, metallic shafts or tubes, reinforced shafts or tubes, or the like including other suitable materials such as those disclosed herein. In some embodiments, the polymeric shaft may be a singular monolithic or unitary member. In some embodiments, the polymeric shaft may include a plurality of portions or segments that are coupled together. The total length of the inner catheter 14 and/or the polymeric shaft may be in the range of about 60 to 150 cm, or about 80 to 120 cm, or about 100 to 115 cm, or about 112±0.02 cm. Just like the outer sheath 12, in some embodiments, the inner catheter 14 and/or the polymeric shaft may be curved, for example adjacent to a distal end thereof. In some embodiments, the polymeric shaft may have one or more sections with a differing hardness/stiffness (e.g., differing shore durometer). For example, the polymeric shaft may have a proximal region and an intermediate region. In some embodiments, the proximal region may include a generally stiff polymeric material such as a 72D polyether block amide (e.g., 72D PEBAX) and may have a length in the range of about 60 to 150 cm, or about 80 to 120 cm, or about 100 to 115 cm, or about 109.5±0.02 cm. In some embodiments, the intermediate region may include a 40D polyether block amide (e.g., 40D PEBAX) and may have a length in the range of about 5 to 25 mm, or about 10 to 20 mm, or about 15±0.01 mm. The decreased outer diameter section may also differ from the proximal region and/or the intermediate region and, in some embodiments, may include a 72D polyether block amide (e.g., 72D PEBAX) and may have a length in the range of about 0.5 to 2 cm (5 to 20 mm), or about 0.8 to 1.5 cm (8 to 15 mm), or about 1±0.001 cm (10±0.01 mm). These are just examples. Other suitable polymers may also be used, such as, but not limited to, other polymers disclosed herein.

In some embodiments, the inner catheter 14 may include a plurality of lumens extending at least partially therethrough. For example, in some embodiments, the inner catheter 14 and/or the polymeric shaft may include a first lumen, a second lumen, a third lumen, and/or a fourth lumen. In general, the lumens extend along the entire length of the inner catheter 14 and/or the polymeric shaft. Other embodiments are contemplated, however, where one or more of lumens extend along only a portion of the length of inner catheter 14 and/or the polymeric shaft. For example, the fourth lumen may stop just short of the distal end of the inner catheter 14 and/or the polymeric shaft and/or be filled in at its distal end to effectively end the fourth lumen proximal of the distal end of the inner catheter 14 and/or the polymeric shaft.

Disposed within one of the lumens (e.g., a first lumen) may be one or more push-pull rods (not shown), which are used to expand and/or elongate the medical device implant when the device handle 18 is actuated by connecting a portion of the device handle 18 to the medical device implant to transmit rotational and/or axial motion thereto. In some embodiments, one or more of the lumens (e.g., the first lumen) may be lined with a low friction liner (e.g., a FEP liner). Disposed within a second lumen may be a pin release mandrel (not shown), which in some embodiments may facilitate release of the valve replacement implant 16. In some embodiments, the second lumen may be lined with a hypotube liner. In some embodiments, a third lumen may be a guidewire lumen. In some embodiments, the third lumen may be lined with a hypotube liner. In some embodiments, a fourth lumen may be used to house a non-stretch wire or member. The form of the non-stretch wire or member may vary. In some embodiments, the non-stretch wire or member may take the form of a stainless steel braid. The non-stretch wire or member may optionally include a pair of longitudinally-extending aramid and/or para aramid strands (for example, KEVLAR®) disposed on opposite sides of the braid. In general, rather than being "disposed within" the fourth lumen, the non-stretch wire or member may be embedded within the fourth lumen and/or the polymeric shaft. In addition, the non-stretch wire or member may extend to a position adjacent to the distal end portion but not fully to the distal end of the inner catheter 14 and/or the polymeric shaft. For example, a short distal segment of the fourth lumen may be filled in with polymer material adjacent to the distal end of inner catheter 14 and/or the polymeric shaft.

Figure 2:
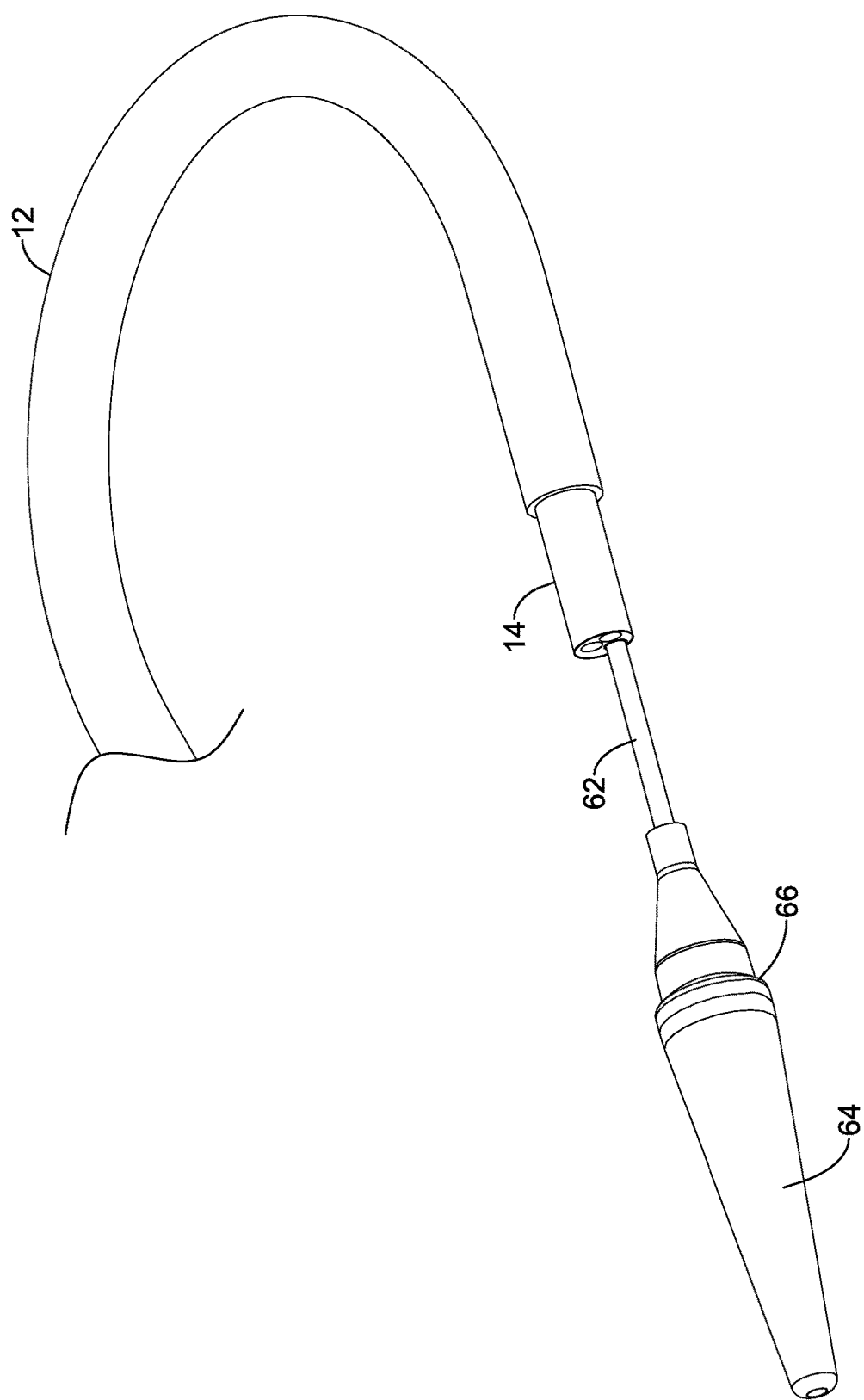
FIG. 2 is a partial perspective view of a portion of the example valve delivery system of FIG. 1.

In some embodiments, the valve delivery system 10 may include a tubular extension 62 extending distally from a distal end of the inner catheter 14, as seen in FIG. 2 for example. In some embodiments, the tubular extension 62 may be axially movable and/or translatable relative to the inner catheter 14. In some embodiments, a nose cone 64 may be fixedly attached to the tubular extension 62 at a distal end of the tubular extension 62. The nose cone 64 generally may be designed to have an atraumatic shape. In some embodiments, a proximal portion of the nose cone 64 may be configured to matingly engage a distal end of the outer sheath in the first position, and in some embodiments, the nose cone 64 may include a ridge 66 that is configured to abut the distal end or distal tip of the outer sheath 12 in the first position, such as during delivery of the valve replacement implant 16 for example. As readily seen in the Figures, in some embodiments, the valve replacement implant 16 may be disposed about and/or may surround the tubular extension 62.

Figure 6:
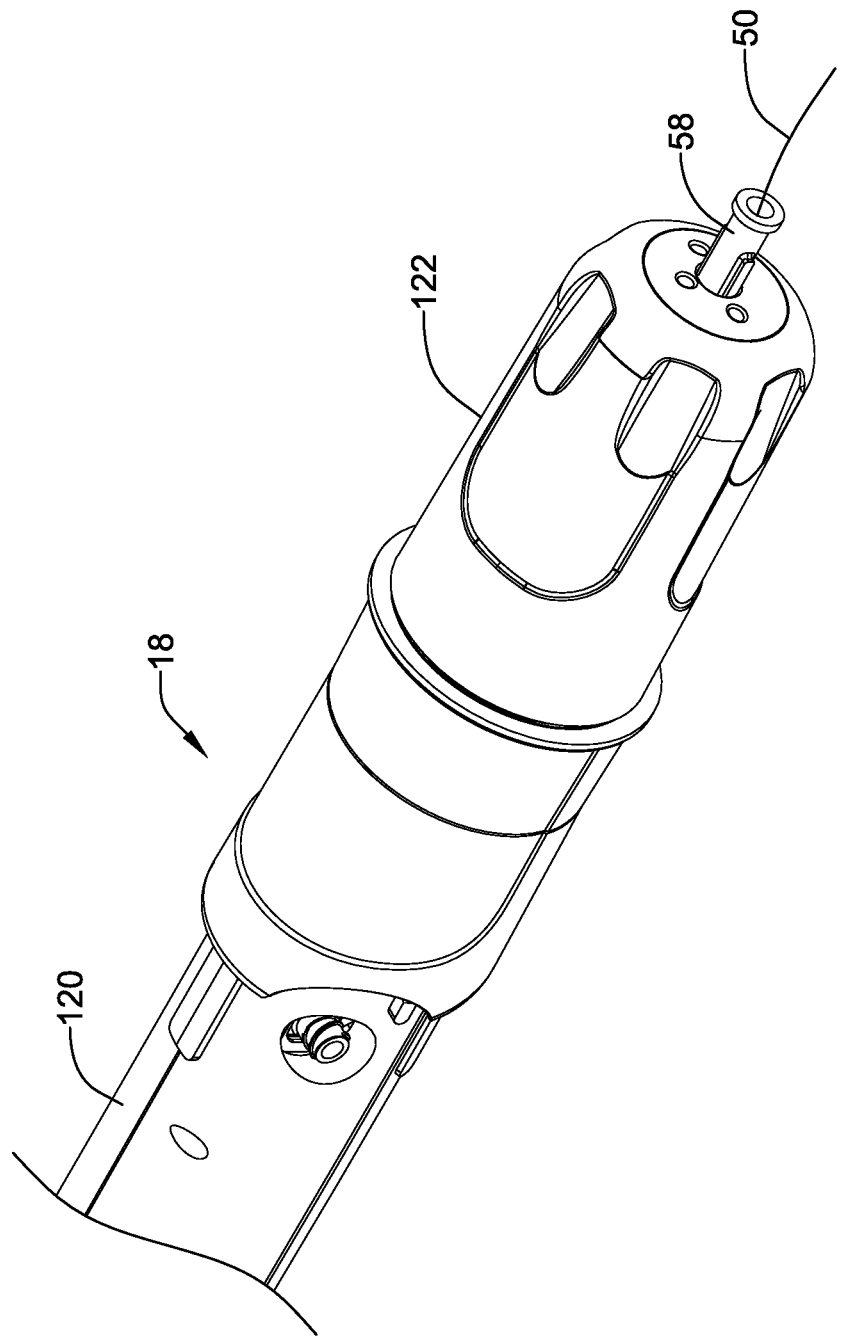
FIG. 6 is a partial perspective view of a portion of the example valve delivery system of FIG. 1.
Figure 7:
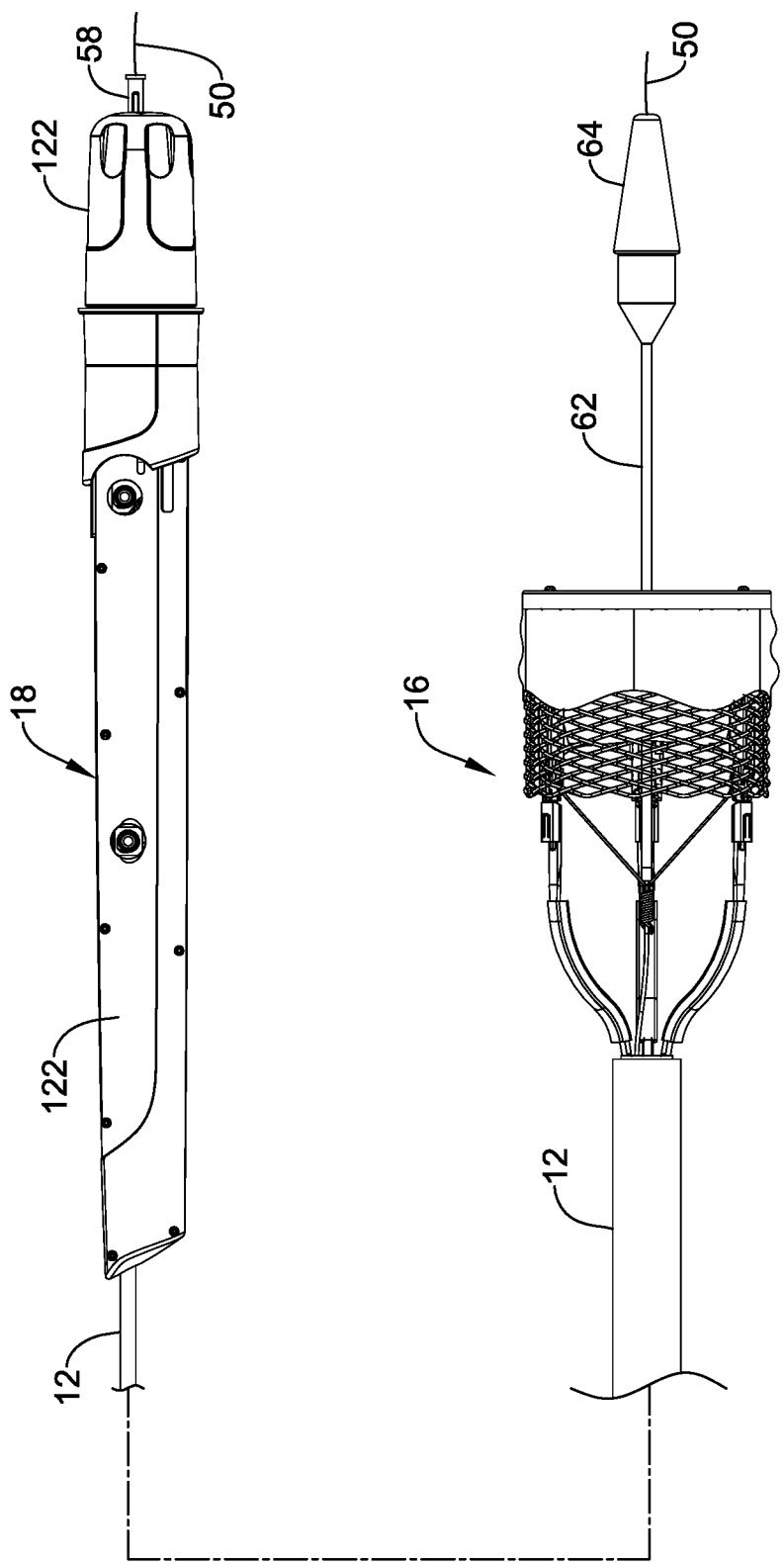
FIGS. 7-8 illustrate movement of a nosecone subassembly in a side view of the example valve delivery system of FIG. 1.
Figure 8:
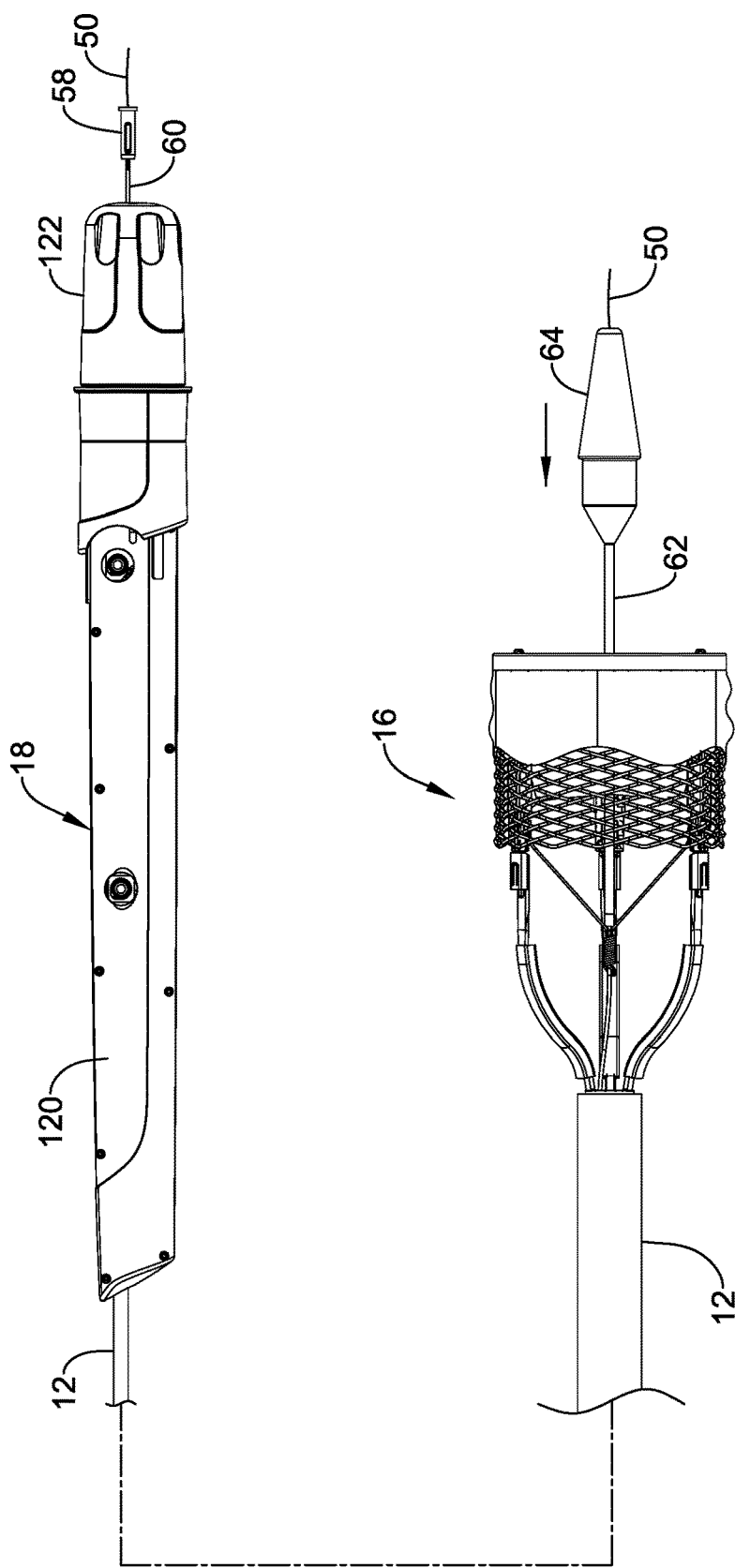

In some embodiments, the tubular extension 62 may be fixedly attached to a hypotube 60 slidably received within one of the plurality of lumens of the inner catheter 14. In some embodiments, a luer connector 58 may be attached to a proximal end of the hypotube 60. In some embodiments, the luer connector 58 may be configured to engage a proximal end of the device handle 18, as seen in FIG. 6 for example. In some embodiments, the luer connector 58, the hypotube 60, the tubular extension 62, and the nose cone 64 may together form a nose cone subassembly having a guidewire lumen extending therethrough, and thus may define a guidewire lumen extending through the percutaneous valve delivery system 10. In some embodiments, the guidewire lumen may be configured to slidably receive a guidewire 50 therein, as seen in FIGS. 6-8.

Figure 9:
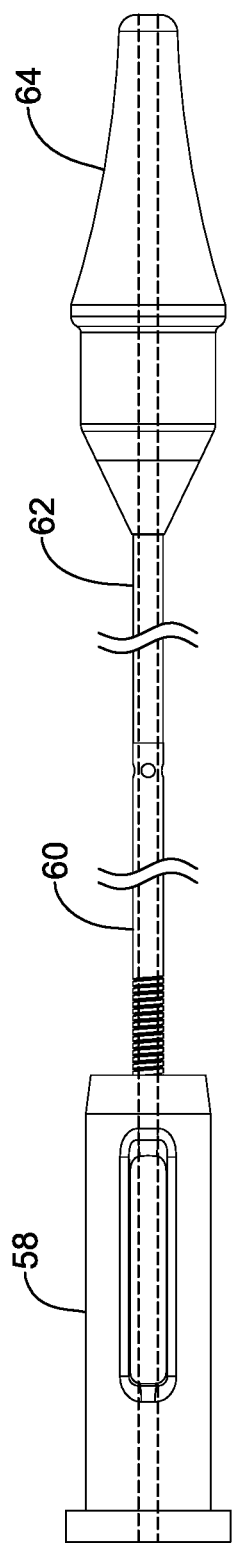
FIG. 9 is a side view of an example nosecone subassembly.

FIG. 9 illustrates an example nose cone subassembly including a luer connector 58, a hypotube 60, a tubular extension 62, and a nose cone 64, the nose cone subassembly having a guidewire lumen extending therethrough. In some embodiments, the luer connector 58 may be threadably attached to the proximal end of the hypotube 60. In some embodiments, a distal end of the hypotube 60 may be fixedly attached to a proximal end of the tubular extension 62, such that an axial lumen of the hypotube 60 is in fluid communication with an axial lumen of the tubular extension 62, thereby forming at least a central portion of the guidewire lumen of the nose cone subassembly. In some embodiments, the nose cone subassembly may be axially movable, translatable, and/or actuatable relative to the inner catheter 14 and/or the device handle 18. In some embodiments, the nose cone 64 may include a lumen extending therethrough and in fluid communication with the lumen of the tubular extension 62 so as to form a distal portion of the guidewire lumen.

Figure 10:
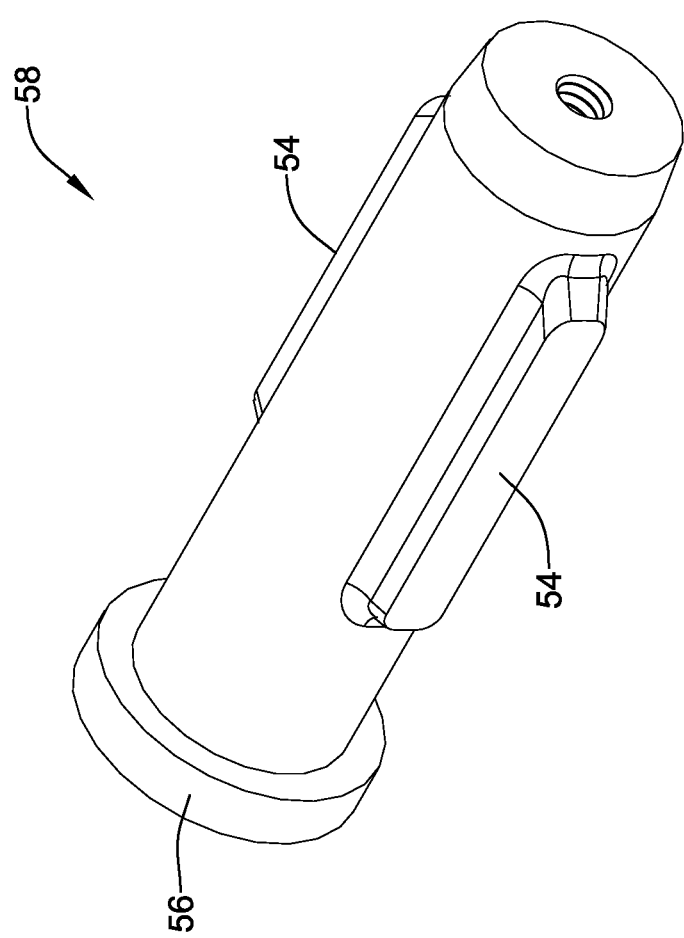
FIG. 10 is a perspective view of a portion of the example nosecone subassembly of FIG. 9.

FIG. 10 illustrates an example luer connector 58 having a generally elongated tubular body. In some embodiments, the luer connector 58 may include a protrusion 56 disposed at or adjacent to, and extending radially outward from, a proximal end of the luer connector 58. In some embodiments, the protrusion 56 may be an annular or ring-like protrusion. In at least some embodiments, the protrusion 56 may prevent distal axial movement of the luer connector 58, and therefore the nose cone subassembly to which the luer connector 58 is attached, past the proximal end of the device handle 18 and/or the rotatable control knob 122. In some embodiments, the protrusion 56 may be configured to engage with and/or abut the proximal end of the device handle 18 and/or a corresponding mating recess in the proximal end of the device handle 18 and/or the rotatable control knob 122. In some embodiments, the luer connector 58 may include one or more guide bars 54 extending generally parallel to a central axis of the luer connector 58 and extending laterally outward from an outer surface of the elongated tubular body of the luer connector 58. In some embodiments, the one or more guide bars 54 may permit the luer connector 58 to slidingly engage the device handle 18 while preventing rotational movement of the luer connector 58 relative to the device handle 18 when the one or more guide bars 54 is engaged with the device handle 18. In some embodiments, the one or more guide bars 54 may permit the luer connector 58 to slidingly engage the device handle 18 while also permitting rotational movement of the luer connector 58 relative to the device handle 18 when the one or more guide bars 54 is engaged with the device handle. In some embodiments, the one or more guide bars 54 may form a helical or spiral configuration enabling the luer connector 58 to be removably threaded or screwed into the proximal end of the device handle 18 to prevent axial movement or translation of the nose cone subassembly when the luer connector 58 is engaged with the device handle 18.

Figure 11:
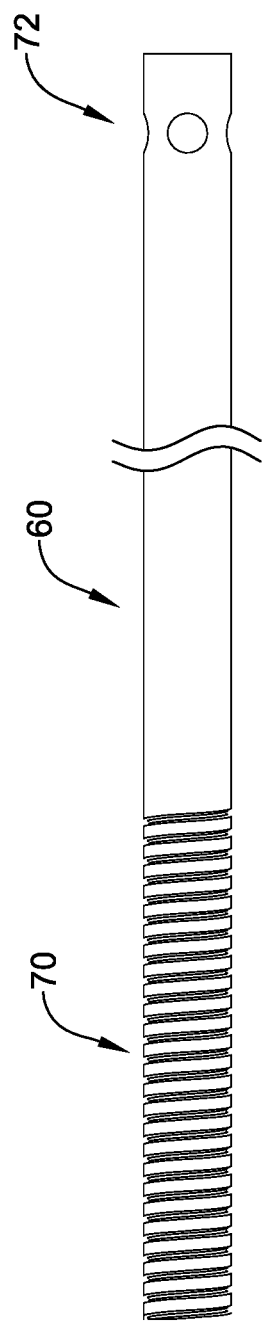
FIG. 11 is a side view of a portion of the example nosecone subassembly of FIG. 9.

FIG. 11 illustrates an example hypotube 60. In some embodiments, the hypotube 60 may include a lumen extending therethrough. In some embodiments, the hypotube 60 may include an externally threaded proximal end 70 configured to threadably engage an internally threaded lumen of the luer connector 58. In some embodiments, the lumen of the hypotube 60 may be in fluid communication with the lumen of the luer connector 58 so as to form a proximal portion of the guidewire lumen of the nose cone subassembly. In some embodiments, the hypotube 60 may include a plurality of apertures 72 extending laterally through a side wall of the hypotube 60 adjacent to a distal end of the hypotube 60. In some embodiments, the plurality of apertures 72 may be regularly or evenly spaced about the circumference of the hypotube 60. In some embodiments, the plurality of apertures 72 may be irregularly or unevenly spaced about the circumference of the hypotube 60. In at least some embodiments, the plurality of apertures may be configured to engage with and/or receive one or more portions of the tubular extension 62 therein to form a mechanical connection fixedly attaching the hypotube 60 to the tubular extension 62. In some embodiments, each of the plurality of apertures may engage or receive one portion of the tubular extension 62 extending radially outward from an outer surface of the tubular extension 62. In some embodiments, the lumen of the hypotube 60 may be in fluid communication with a lumen of the tubular extension 62 so as to form a central portion of the guidewire lumen of the nose cone subassembly.

As can be seen in FIGS. 3-5, the device handle 18 includes a handle housing 120. In some embodiments, the device handle 18 may also include a rotatable control knob 122 disposed on or about the handle housing 120 (e.g., at a proximal end of the handle housing 120) and may be used to move one or more of the components of the valve delivery system 10 (e.g., the outer sheath 12, the push-pull rods, the pin release mandrel, etc.). In some embodiments, the device handle 18 may include a rotatable collar 156 disposed about the handle housing 120. In some embodiments, the rotatable collar 156 may be disposed adjacent the rotatable control knob 122. In some embodiments, the rotatable control knob 122 may be disposed about a proximal portion of the rotatable collar 156. In some embodiments, a slidable door 124 may also be disposed about the handle housing 120. In some embodiments, the slidable door 124 may translate distally to expose a distal portion of the rotatable collar 156 which may be positioned generally under the slidable door 124. In some embodiments, the rotatable collar 156 may be rotated to move one or more components of the valve delivery system 10. In some embodiments, the device handle 18 may also include one or more apertures and/or flush ports that can be used to flush the valve delivery system 10. In some embodiments, a distal flush port and a proximal flush port may be accessible from an exterior of the handle housing 120 through a distal aperture and a proximal aperture, respectively.

FIGS. 4 and 5 illustrate a side view of the device handle 18 with a portion of the handle housing 120 removed, exposing at least some of the interior components. Here it can be seen that the outer sheath 12 may be fixedly attached to a sheath adapter. The sheath adapter may be attached to a sheath carriage, which may be threaded onto a lead screw. The distal flush port may be disposed on the sheath adapter. In general, the distal flush port provides access to the interior or lumen of the outer sheath 12 (e.g., access to space between the inner catheter 14 and the outer sheath 12) so that a clinician can flush fluid through the lumen of the outer sheath 12 to remove any unwanted materials (e.g., air, fluid, contaminants, etc.) therein prior to use of the valve delivery system 10. In at least some embodiments, the distal flush port has a luer type connector (e.g., a one-way luer connector) that allows a device such as a syringe with a corresponding connector to be attached thereto for flushing.

Extending through and proximally from the sheath adapter is the inner catheter 14. A proximal end of the inner catheter 14 is selectively attached (e.g., releasably locked) to a diverter block. The diverter block may be attached to a support body. The proximal flush port may be disposed on the support body and can be used to flush the lumen(s) of the inner catheter 14 and/or the polymeric shaft, and may function similarly to the distal flush port, for example. In general, the diverter block and/or the support body may have one or more passageways or lumens formed therein.

In some embodiments, the push-pull rods and/or the pin release mandrel may extend from a mechanism operatively connected to the rotatable control knob 122, the slidable door 124, and/or the rotatable collar 156 through respective passageways or lumens in the diverter block and/or the support body and into the lumen(s) of the inner catheter 14 and/or the polymeric shaft. Alternatively, the proximal ends of the push-pull rods and/or the pin release mandrel may each be attached to a shaft or hypotube (e.g., solid in cross-section, tubular, etc.), and each of the shafts or hypotubes may extend proximally therefrom through one of the one or more passageways or lumens to the mechanism operatively connected to the rotatable control knob 122, the slidable door 124, and/or the rotatable collar 156. For example, a first shaft or hypotube and a second shaft or hypotube may extend through the passageways or lumens in the diverter block, and in some embodiments, the first shaft or hypotube may extend through a first passageway or lumen and the second shaft or hypotube may extend through a second passageway or lumen that is separate or distinct from the first passageway or lumen. In at least some embodiments, the first shaft may be attached to the pin release mandrel. In at least some embodiments, the second shaft may be attached to the push-pull rods. It should be noted that at in least some embodiments of the valve delivery system 10, three push-pull rods are utilized. In these embodiments, the three push-pull rods may come together (e.g., brought into contact with one another or otherwise brought into relatively close proximity with one another) adjacent to the distal end of the inner catheter 14 and enter the first passageway or lumen. At one or more positions along their length, the push-pull rods may be fixedly attached to one another. For example, in some embodiments, the push-pull rods may be welded together about 10.16 cm (about 4.00 inches) proximally from their distal ends. In some embodiments, the push-pull rods may be welded together proximate their proximal ends in addition to or instead of the distal weld. Proximally thereafter, the push-pull rods may extend to the second shaft.

The device handle 18 is generally configured for coordinated movement of multiple structures of the valve delivery system 10. For example, the device handle 18 is configured to allow a user to move the outer sheath 12 (e.g., relative to the inner catheter 14), move the push-pull rods, and move the pin release mandrel. Moreover, the device handle 18 is configured so that the appropriate structure can be moved at the appropriate time during the intervention so that the valve replacement implant 16 can be delivered in an efficient manner.

To help facilitate the coordinated movement, the device handle 18 may include one or more mechanisms disposed therein which may translate, transfer, and/or convert motion (e.g., rotational motion) of the rotatable control knob 122, the slidable door 124, and/or the rotatable collar 156 into axial motion, movement, and/or translation at a distal end of the valve delivery system 10.

FIGS. 4 and 5 partially illustrate some of the coordinated motion achieved by the device handle 18. It should be noted that some elements of the valve delivery system 10 are not shown in FIGS. 4 and 5 for clarity. For example, FIG. 4 illustrates a first position of the outer sheath 12 relative to inner catheter 14, wherein the nose cone 64 matingly engages a distal end of the outer sheath 12 to fully sheath (e.g., contain) the valve replacement implant 16 within the outer sheath 12 in a delivery configuration. While in this position, the sheath carriage (with the distal flush port) is positioned adjacent to the distal end of the device handle 18. Upon rotation of the rotatable control knob 122 (e.g., in the clockwise direction), the lead screw begins to rotate, causing the sheath carriage to move along the lead screw in the proximal direction, resulting in proximal movement of the outer sheath 12 toward a second position relative to the inner catheter 14 and/or the nose cone 64 (e.g., "unsheathing" the valve replacement implant 16), as seen in FIG. 5 for example.

Eventually, sufficient actuation of the rotatable control knob 122, the slidable door 124, and/or the rotatable collar 156, and the operatively connected mechanism(s) of the device handle 18, may actuate the valve replacement implant 16 from the delivery configuration to the deployed configuration, and may further release and/or detach the valve replacement implant 16 from the inner catheter 14 and/or the valve delivery system 10.

In some cases, during deployment of the valve replacement implant 16, a physician or user of the valve delivery system 10 may find a reason or desire to withdraw the nose cone 64 proximally (i.e., away from a wall of the ventricle and closer to the inner catheter 14). Since the nose cone subassembly may be slidably received within a lumen of the inner catheter 14, and the inner catheter is fixed relative to the device handle 18, proximal withdrawal of the luer connector 58 relative to the device handle 18 will cause a commensurate proximal movement of the nose cone 64 relative to the valve replacement implant 16, as seen in FIGS. 7 and 8 for example.

Following deployment of the valve replacement implant 16, the rotatable control knob 122 may be rotated to move the sheath carriage distally within the handle housing 120, thereby moving the outer sheath 12 from the second position relative to the inner catheter 14 distally to the first position relative to the inner catheter 14 so as to cover or re-sheath the elements of the valve delivery system 10 disposed at the distal end. The valve delivery system 10 may then be removed from the patient's anatomy.

The materials that can be used for the various components of the valve delivery system 10 (and/or other systems and components disclosed herein) and the various tubular members disclosed herein may include those commonly associated with medical devices. For example, in some embodiments, the outer sheath 12, the inner catheter 14, and/or the hypotube 60, (as well as other components disclosed herein) may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the outer sheath 12 and/or the inner catheter 14 may also be doped with, made of, or otherwise include a radiopaque material. Radiopaque materials are understood to be materials capable of producing a relatively bright image on a fluoroscopy screen or another imaging technique during a medical procedure. This relatively bright image may aid the user of the valve delivery system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the valve delivery system 10 to achieve the same result.

In some embodiments, a degree of Magnetic Resonance Imaging (MM) compatibility is imparted into the valve delivery system 10. For example, the outer sheath 12 and/or the inner catheter 14, or portions thereof, may be made of a material that does not substantially distort the image and create substantial artifacts (i.e., gaps in the image). Certain ferromagnetic materials, for example, may not be suitable because they may create artifacts in an MM image. The outer sheath 12 and/or the inner catheter 14, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of the outer sheath 12 and/or the inner catheter 14 that may define a generally smooth outer surface for the valve delivery system 10. In other embodiments, however, such a sheath or covering may be absent from a portion of all of the valve delivery system 10, such that the outer sheath 12 and the inner catheter 14, either individually or together, may form an outer surface. The sheath or covering may be made from a polymer or other suitable material. Some examples of suitable polymers for the sheath or covering, the outer sheath 12, the inner catheter 14, the tubular extension 62, and/or other polymeric components of the valve delivery system may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the valve delivery system 10 (including, for example, the exterior surface of the outer sheath 12 and the inner catheter 14) may be sandblasted, bead blasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over a portion of the outer sheath 12 and/or the inner catheter 14, or other portions of the valve delivery system 10. Alternatively, the sheath may comprise a lubricious, hydrophilic, protective, or other type of coating. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A percutaneous valve delivery system, comprising:
   an outer sheath;
   an inner catheter disposed within the outer sheath, the inner catheter including a plurality of non-concentric lumens formed therein;
   a tubular extension extending distally from a distal end of the inner catheter;
   wherein the tubular extension is axially movable relative to the inner catheter;
   wherein the tubular extension is fixedly attached to and within a hypotube slidably received within one of the plurality of lumens;
   a nose cone attached to the tubular extension;
   a handle attached to the outer sheath, wherein the handle is configured to shift the outer sheath between a first position and a second position relative to the inner catheter; and
   a valve replacement implant releasably coupled to the inner catheter.

2. The percutaneous valve delivery system of claim 1, further comprising a luer connector attached to a proximal end of the hypotube, the luer connector being configured to engage a proximal end of the handle.

3. The percutaneous valve delivery system of claim 2, wherein the luer connector, the hypotube, the tubular extension, and the nose cone together form a nose cone subassembly having a guidewire lumen extending through the percutaneous valve delivery system, wherein the guidewire lumen is configured to slidably receive a guidewire therein.

4. The percutaneous valve delivery system of claim 2, wherein the luer connector is threadably attached to the proximal end of the hypotube.

5. The percutaneous valve delivery system of claim 2, wherein the luer connector includes a protrusion preventing distal axial movement of the luer connector past the proximal end of the handle.

6. The percutaneous valve delivery system of claim 2, wherein the nose cone subassembly is axially movable relative to the inner catheter and the handle.

7. The percutaneous valve delivery system of claim 1, wherein the valve replacement implant is disposed about the tubular extension.

8. The percutaneous valve delivery system of claim 1, wherein the nose cone is fixedly attached at a distal end of the tubular extension.

9. The percutaneous valve delivery system of claim 1, wherein a proximal portion of the nose cone is configured to matingly engage a distal end of the outer sheath in the first position.

10. A percutaneous valve delivery system, comprising:
an outer sheath;
an inner catheter disposed within the outer sheath, the inner catheter including a plurality of non-concentric lumens formed therein;
a tubular extension extending distally from a distal end of the inner catheter;
wherein the tubular extension is axially movable relative to the inner catheter;
wherein the tubular extension is fixedly attached to and within a hypotube slidably received within one of the plurality of lumens;
a nose cone attached to the tubular extension;
a handle attached to the outer sheath, wherein the handle is configured to shift the outer sheath between a first position and a second position relative to the inner catheter, the inner catheter being fixed to the handle; and
a valve replacement implant releasably coupled to the inner catheter, the tubular extension extending through the valve replacement implant.

11. The percutaneous valve delivery system of claim 10, further comprising a luer connector attached to a proximal end of the hypotube, the luer connector being configured to engage a proximal end of the handle.

12. The percutaneous valve delivery system of claim 11, wherein the luer connector, the hypotube, the tubular extension, and the nose cone together form a nose cone subassembly having a guidewire lumen extending through the percutaneous valve delivery system, wherein the guidewire lumen is configured to slidably receive a guidewire therein.

13. The percutaneous valve delivery system of claim 11, wherein the luer connector is threadably attached to the proximal end of the hypotube.

14. The percutaneous valve delivery system of claim 11, wherein the luer connector includes a protrusion preventing distal axial movement of the luer connector past the proximal end of the handle.

15. The percutaneous valve delivery system of claim 11, wherein the nose cone subassembly is axially movable relative to the inner catheter and the handle.

16. The percutaneous valve delivery system of claim 10, wherein the nosecone is fixedly attached at a distal end of the tubular extension.

17. The percutaneous valve delivery system of claim 10, wherein a proximal portion of the nose cone is configured to abut a distal end of the outer sheath in the first position.

18. The percutaneous valve delivery system of claim 17, wherein the nose cone is spaced distally from the outer sheath in the second position.

* * * * *